United States Patent
Peddy et al.

(10) Patent No.: US 9,655,885 B2
(45) Date of Patent: *May 23, 2017

(54) AMORPHOUS MIRABEGRON AND PROCESSES FOR CRYSTAL FORMS OF MIRABEGRON

(71) Applicant: DR. REDDY'S LABORATORIES LTD., Hyderabad (IN)

(72) Inventors: Vishweshwar Peddy, Hyderabad (IN); Rajesham Boge, Hyderabad (IN); Yogesh S Gattani, Dist:-Akola (IN); Nagoji Shinde, District—Nanded (IN); Pradip Kumar Ghosh, Dist—Midnapur (IN); Sritharan Seetharaman, Hyderabad (IN); Navin Vaya, Hyderabad (IN); Vaibhav Sihorkar, Hyderabad (IN); Rajashekhar Totad, Hyderabad (IN); Krishna Venkatesh, Hyderabad (IN); Ganesh Arun Katkar, Pune (IN); Snehalatha Movva, Hyderbad (IN); Piyush Chudiwal, Dist—Nasik (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,070

(22) Filed: Apr. 21, 2015

(65) Prior Publication Data

US 2015/0224087 A1 Aug. 13, 2015

Related U.S. Application Data

(63) Continuation-in-part of application No. 14/117,569, filed as application No. PCT/IN2012/000356 on May 17, 2012, now Pat. No. 9,283,210.

(60) Provisional application No. 61/502,911, filed on Jun. 30, 2011.

(30) Foreign Application Priority Data

May 18, 2011 (IN) ............ 1678/CHE/2011

(51) Int. Cl.
*C07D 277/40* (2006.01)
*A61K 31/426* (2006.01)
*A61K 9/14* (2006.01)
*A61K 9/16* (2006.01)

(52) U.S. Cl.
CPC ............ *A61K 31/426* (2013.01); *A61K 9/146* (2013.01); *A61K 9/1635* (2013.01); *C07D 277/40* (2013.01); *C07B 2200/13* (2013.01)

(58) Field of Classification Search
CPC ........................... C07D 277/40; A61K 31/426
See application file for complete search history.

(56) References Cited

U.S. PATENT DOCUMENTS

| | | | |
|---|---|---|---|
| 6,346,532 B1 | 2/2002 | Maruyama et al. | |
| 7,342,117 B2 | 3/2008 | Kawazoe et al. | |
| 9,283,210 B2* | 3/2016 | Peddy .................. | C07D 277/40 |
| 2006/0115540 A1 | 6/2006 | Takasu et al. | |

OTHER PUBLICATIONS

International Search Report dated Nov. 15, 2012, for corresponding International Patent Application No. PCT/IN2012/000356.
Written Opinion dated Nov. 15, 2012, for corresponding International Patent Application No. PCT/IN2012/000356.
"Alzheimer's Disease and Other Forms of Dementia", Dementia—WebMD: Types, Stages, Causes, Symptoms, Treatments, Alzheimer's Disease Health Center, retrieved Online from the Internet on Jan. 26, 2015, pp. 1 to 4, WebMD, LLC, Source—American Association of Family Physicians, URL—http://www.webmd.com/alzheimers/guide/alzheimers-dementia.
Nabili et al., "Overactive Bladder: Facts for Men, Women, and Children", MedicineNet.com, retrieved Online from the Internet on Jan. 26, 2015, pp. 1 to 6, MedicineNet, Inc. URL—http://www.medicinenet.com/script/main/art.asp?articlekey=18300.
Non-Final Office Action mailed by the USPTO on Jan. 28, 2015, for U.S. Appl. No. 14/117,569.

* cited by examiner

*Primary Examiner* — Golam M M Shameem
(74) *Attorney, Agent, or Firm* — Pergament and Cepeda LLP; Milagros A. Cepeda; Edward D. Pergament

(57) ABSTRACT

Aspects of the present invention relate to amorphous form of mirabegron, amorphous solid dispersion of mirabegron, process for its preparation, processes for preparation of α form crystal and β form crystal of mirabegron and pharmaceutical composition thereof.

11 Claims, 3 Drawing Sheets

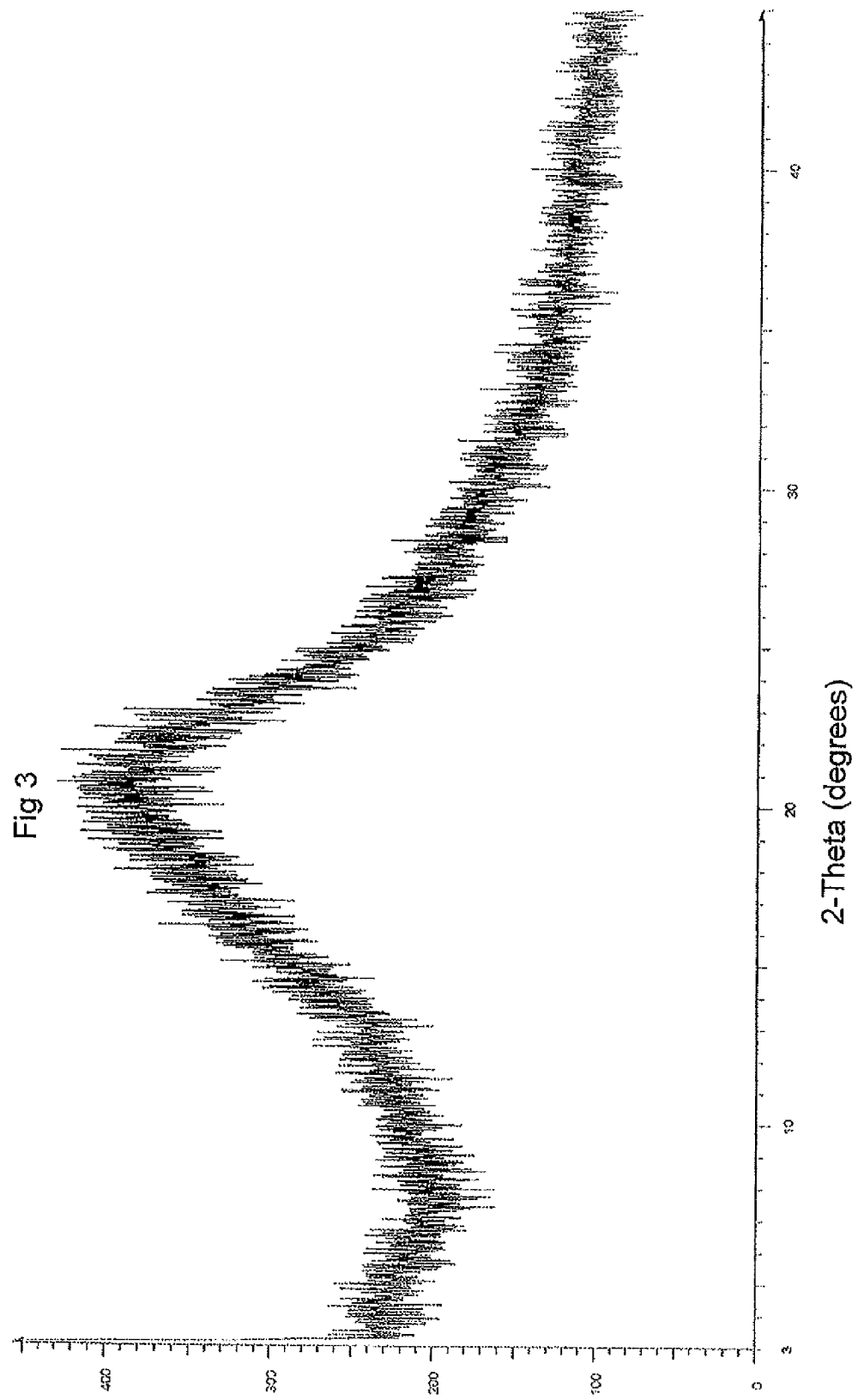

AMORPHOUS MIRABEGRON AND PROCESSES FOR CRYSTAL FORMS OF MIRABEGRON

This application is a Continuation in part of U.S. application Ser. No. 14/117,569, filed Nov. 13, 2013, which is a National Stage Application under 35 U.S.C. §371 of PCT International Application No. PCT/IN2012/000356 filed May 17, 2012, which claims the benefit of U.S. Provisional Application No. 61/502,911, filed Jun. 30, 2011 and Indian Provisional Application No. 1678/CHE/2011, filed on May 18, 2011, all of which are hereby incorporated by reference in their entireties.

INTRODUCTION

Aspects of the present invention relate to amorphous form of mirabegron, amorphous solid dispersion of mirabegron, process for its preparation, processes for the preparation of α-form crystal and β-form crystal of mirabegron and pharmaceutical composition comprising thereof.

BACKGROUND

Mirabegron is chemically described as (R)-2-(2-aminothiazol-4-yl)-4'-[2-[(2-hydroxy-2-phenylethyl)amino]ethyl]-acetanilide or 2-amino-N-[4-[2-[[(2R)-2-hydroxy-2-phenylethyl]amino]ethyl]phenyl]-4-thiazoleacetamide. It has the structure of formula (I).

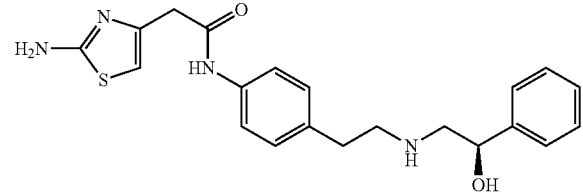

(I)

Mirabegron is an orally active beta-3 adrenoceptor agonist and is under pre-registration in USA and Europe for the potential treatment of urinary frequency, urinary incontinence, or urgency associated with overactive bladder by Astellas Pharma. Mirabegron is approved in Japan. U.S. Pat. No. 6,346,532 B1 discloses mirabegron or a salt thereof and process for its preparation. U.S. Pat. No. 7,342,117 B2 discloses α-form crystal and β-form crystal of mirabegron.

Amorphous forms can be thought of as liquids that have been solidified by the removal of thermal energy or a solvent, in a manner that circumvents crystallization. The amorphous form can have different solubility, stability, and mechanical behavior that can be exploited by pharmaceutical scientists. The solubility of a given solid is a sum of crystal packing energy, cavitation, and solvation energy. Different crystalline forms of a given drug will have different crystal packing energies. The amorphous forms of the same drug require minimal packing energy disruption when dissolving due to absence of an ordered crystal lattice. Thus, the amorphous forms provide the maximal solubility advantage as compared to the crystalline forms of a drug. The 'apparent solubility' and dissolution advantage offered by these systems is a vital approach to enhance bioavailability of poorly water soluble drugs.

There always remains a need to provide the new polymorphic forms of mirabegron and processes for making the new polymorphic forms.

The present invention provides new polymorphic forms of mirabegron which can be used in the pharmaceutical composition.

The present invention provides amorphous mirabegron and amorphous solid dispersion of mirabegron having high stability and physical integrity, e.g. during storage, handling, packaging and the like.

U.S. Pat. No. 7,342,117 B2 discloses the preparation of α-form crystal and β-form crystal of mirabegron.

The methods for the preparation of α-form crystal and β-form crystal of mirabegron as per the literature involves the use of rapid cooling, use of seed material and use of solvents water and ethanol only.

The methods for the preparation of α-form crystal and β-form crystal of mirabegron described in the literature suffer from one or more drawbacks such as reproducibility, use of seed material, less yield, limited solvents, which does not result an industrially feasible process.

Therefore, there is a need to provide simple, reproducible, environment friendly, cost effective, industrially feasible processes for the preparation of α-form crystal and β-form crystal of mirabegron.

SUMMARY

In an aspect, the present invention provides an amorphous form of mirabegron.

In an aspect, the present invention provides an amorphous form of mirabegron characterized by a powder X-ray diffraction (PXRD) pattern, substantially as illustrated by FIG. 1.

In an aspect, the present invention provides a process for the preparation of an amorphous form of mirabegron, comprising:
a) providing a solution of mirabegron in a solvent or mixture of solvents;
b) removing the solvent from the solution obtained in step a), and
c) isolating an amorphous form of mirabegron.

In an aspect, the present invention provides a pharmaceutical composition comprising amorphous form of mirabegron along with one or more pharmaceutically acceptable carriers, excipients, or diluents.

In an aspect, the present invention provides amorphous mirabegron stabilized using one or more of amorphous silica.

In an aspect, the present invention provides solid dispersion of amorphous mirabegron together with one or more pharmaceutically acceptable carriers.

In an aspect, the present invention provides solid dispersion of amorphous mirabegron together with povidone.

In an aspect, the present invention provides solid dispersion of amorphous mirabegron together with copovidone.

In an aspect, the present invention provides solid dispersion of amorphous mirabegron together with hypromellose acetate succinate.

In an aspect the present invention provides solid dispersion of amorphous mirabegron together with hydroxylpropyl cellulose.

In an aspect the present invention also provides amorphous mirabegron and amorphous solid dispersion of mirabegron further comprising an antioxidant.

In an aspect, the present invention provides solid dispersion of amorphous mirabegron together with povidone characterized by a powder X-ray diffraction (PXRD) pattern, substantially as illustrated by FIG. 2. or FIG. 3.

In an aspect, the present invention provides a process for preparing a solid dispersion of amorphous mirabegron together with one or more pharmaceutically acceptable carriers, comprising:
a) providing a solution or suspension of mirabegron in combination with one or more pharmaceutically acceptable carriers in a solvent or mixture of solvents;
b) removing the solvent from the solution or suspension obtained in step a) or combining the solution obtained in step a), with an anti-solvent, and
c) isolating solid dispersion of amorphous mirabegron together with one or more pharmaceutically acceptable carrier.

In an aspect, the present invention provides a process for preparing a solid dispersion of amorphous mirabegron together with one or more pharmaceutically acceptable carriers, comprising:
a) blending mirabegron and at least one carrier selected form copovidone, povidone, methyl cellulose, hypromellose acetate succinate, polyethylene oxide, polyethylene glycol and one or more other pharmaceutically acceptable excipients;
b) heating the blend of step a) to form a molten slurry;
c) extruding the slurry of step b);
d) milling the extrudates of step c).

In an aspect, the present invention provides a process for preparing amorphous mirabegron or solid dispersion of amorphous mirabegron together with one or more pharmaceutically acceptable carriers, comprising:
a) providing a solution or suspension of mirabegron in combination with amorphous silica and one or more pharmaceutically acceptable carriers in a solvent or mixture of solvents;
b) spraying the mixture of step a) on a suitable substrate in a fluidized bed processor or top spray granulator;
c) drying the mass till desired loss on drying (LOD) is achieved.

In an aspect, the present invention provides a process for preparing a solid dispersion of amorphous mirabegron together with one or more pharmaceutically acceptable carriers, comprising:
a) providing a solution or suspension of mirabegron in combination with one or more pharmaceutically acceptable carriers and antioxidant in a solvent or mixture of solvents;
b) removing the solvent from the solution or suspension obtained in step a) or combining the solution obtained in step a), with an anti-solvent, and
c) isolating solid dispersion of amorphous mirabegron together with one or more pharmaceutically acceptable carrier.

In an aspect, the present invention provides a process for the preparation of α-form crystal of mirabegron comprising:
a) providing a solution of mirabegron in a solvent selected from methanol, ethanol, tetrahydrofuran, ethyl acetate, toluene or mixtures thereof;
b) cooling the solution obtained in step a), and
c) isolating α-form crystal of mirabegron.

In an aspect, the present invention provides a process for the preparation of α-form crystal of mirabegron, comprising:
a) dissolving mirabegron in a mixture of methanol and water to provide a solution;
b) cooling the solution obtained in step a), and
c) isolating α-form crystal of mirabegron.

In an aspect, the present invention provides a process for the preparation of α-form crystal of mirabegron, comprising:
a) providing a solution of mirabegron in a solvent selected from tetrahydrofuran, methanol, ethanol, acetone, acetonitrile, 1,4-dioxane, methyl isobutyl ketone, chlorobenzene or mixtures thereof;
b) adding an anti-solvent to the solution of step a), selected from cyclohexane, methylcyclohexane, n-heptane, diisopropyl ether, methyl tertiary butyl ether, toluene, water, provided that when methanol is used as a solvent then anti-solvent is other than water; and
c) isolating α-form crystal of mirabegron.

In an aspect, the present invention provides a process for the preparation of α-form crystal of mirabegron comprising:
a) dissolving mirabegron in acetone to provide a solution;
b) adding the solution obtained from step a) to methylcyclohexane, and
c) isolating α-form crystal of mirabegron.

In an aspect, the present invention provides a process for the preparation of α-form crystal of mirabegron comprising:
a) providing a solution of mirabegron in a solvent or mixture of solvents, and
b) isolating α-form crystal of mirabegron by the slow solvent evaporation.

In an aspect, the present invention provides a process for the preparation of β-form crystal of mirabegron comprising:
a) dissolving mirabegron in methyl isobutyl ketone to provide a solution;
b) cooling the solution obtained in step a), and
c) isolating β-form crystal of mirabegron.

In an aspect, the present invention provides a process for the preparation of β-form crystal of mirabegron comprising:
a) providing a solution of mirabegron in a solvent selected from tetrahydrofuran, formamide, N,N-dimethylformamide, N,N-dimethylacetamide, 2-methoxyethanol, morpholine or mixtures thereof;
b) adding the solution obtained from step a) to an anti-solvent selected from methylcyclohexane, n-heptane, toluene, water, and
c) isolating β-form crystal of mirabegron.

In an aspect, the present invention provides a process for the preparation of β-form crystal of mirabegron comprising:
a) providing a solution of mirabegron in a solvent selected from dimethylsulfoxide, morpholine, N-methylpyrolidone, ethyl acetate, or mixtures thereof;
b) adding an anti-solvent to the solution obtained from step a) selected from the group of n-heptane and water, and
c) isolating β-form crystal of mirabegron.

In an aspect, the present invention provides a process for the preparation of β-form crystal of mirabegron comprising:
a) dissolving mirabegron in methanol to provide a solution;
b) adding water to the solution obtained in step a)
c) isolating β-form crystal of mirabegron.

In an aspect, the present invention provides pharmaceutical formulations comprising solid dispersions of amorphous mirabegron together with one or more pharmaceutically acceptable excipients.

In an aspect, the present invention provides pharmaceutical formulations comprising amorphous mirabegron or solid dispersions of amorphous mirabegron together with at least one antioxidant and one or more pharmaceutically acceptable excipients.

In as aspect, the present invention provides a method for the treatment of a disease associated with overactive bladder in a patient comprising administering a therapeutically effective amount of the α-form crystal of mirabegron obtained according to the present invention together with at least one pharmaceutically acceptable carrier.

In as aspect, the present invention provides a method for the treatment of a disease associated with overactive bladder in a patient comprising administering a therapeutically effective amount of amorphous solid dispersion of mirabegron together with at least one pharmaceutically acceptable carrier.

BRIEF DESCRIPTION OF THE DRAWINGS

FIG. 3 is an illustration of a powder X-ray diffraction (PXRD) pattern of solid dispersion of amorphous mirabegron prepared according to Example 3.

DETAILED DESCRIPTION

In an aspect, the present invention provides an amorphous form of mirabegron.

Figure 1:
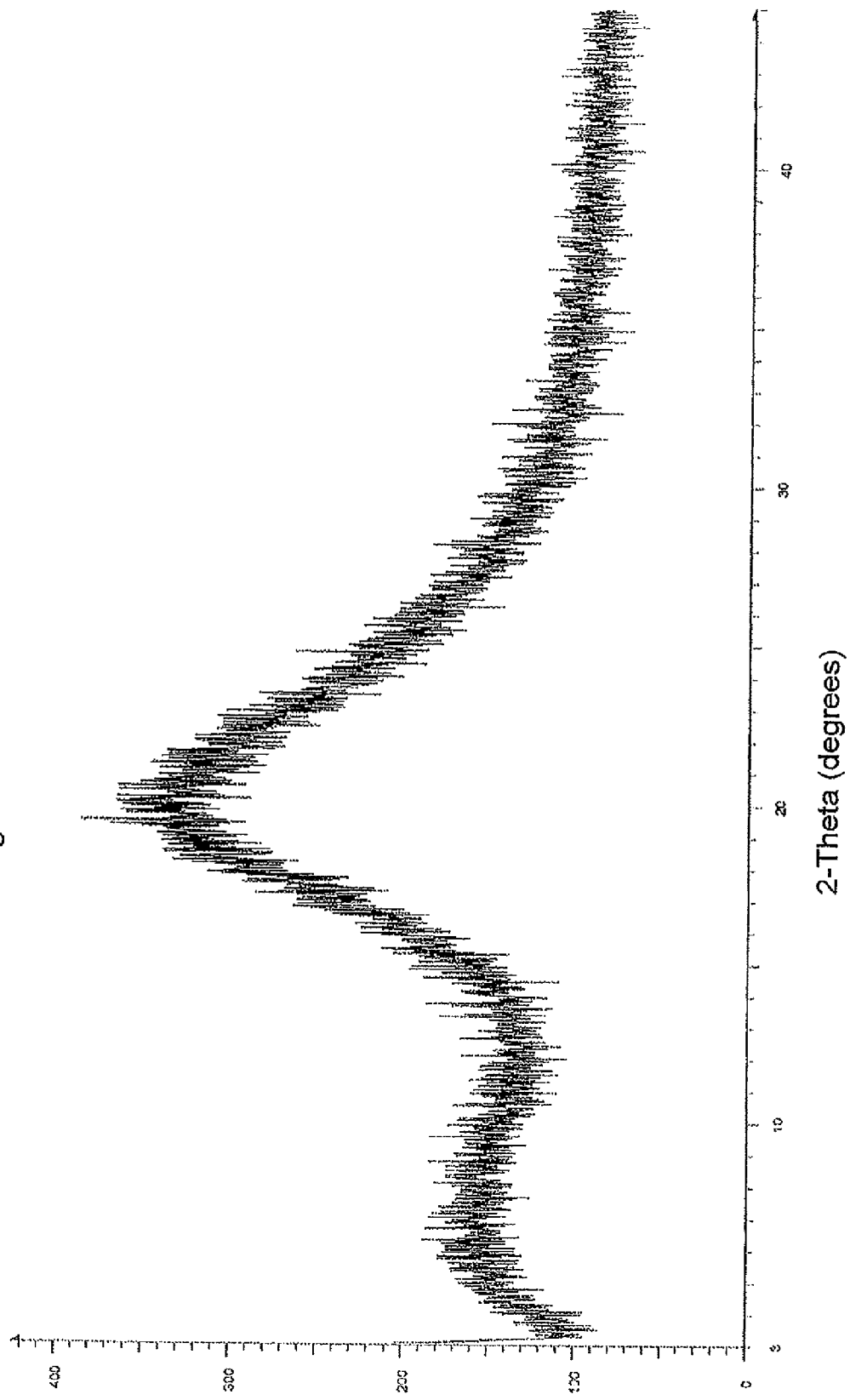
FIG. 1 is an illustration of a powder X-ray diffraction (PXRD) pattern of an amorphous form of mirabegron prepared according to Example 1.

In an aspect, the present invention provides an amorphous form of mirabegron characterized by a powder X-ray diffraction (PXRD) pattern, substantially as illustrated by FIG. 1.

In an aspect, the present invention provides a process for the preparation of an amorphous form of mirabegron, comprising:
 a) providing a solution of mirabegron in a solvent or mixture of solvents;
 b) removing the solvent from the solution obtained in step a), and
 b) isolating an amorphous form of mirabegron.

Step a) involves providing a solution of mirabegron in a solvent or mixture of solvents. Providing a solution in step a) includes:
 i) solutions obtained from reaction mixtures in the final stage of processes for preparing the mirabegron or
 ii) dissolving mirabegron in a suitable solvent or mixture of solvents.

Suitable solvents that may be used in step a) include, but are not limited to, alcohol solvents; ketone solvents; halogenated hydrocarbon solvents; ester solvents; nitrile solvents; polar aprotic solvents; water; or mixtures thereof.

The dissolution temperatures may range from about 0° C. to about the reflux temperature of the solvent, depending on the solvent used for dissolution, as long as a clear solution of mirabegron is obtained without affecting its quality. The solution may optionally be treated with carbon, flux-calcined diatomaceous earth (Hyflow), or any other suitable material to remove color and/or to clarify the solution.

Optionally, the solution obtained above may be filtered to remove any insoluble particles. The solution may be filtered by passing through paper, glass fiber, or other membrane material, or a bed of a clarifying agent such as Celite® or Hyflow. Depending upon the equipment used and the concentration and temperature of the solution, the filtration apparatus may need to be preheated to avoid premature crystallization.

Step b) involves the removal of solvents from the solution obtained from step a). Suitable techniques which may be used for the removal of the solvent include using a rotational distillation device such as a Büchi® Rotavapor®, spray drying, agitated thin film drying, freeze drying (lyophilization), and the like, or any other suitable technique.

The solvent may be removed, optionally under reduced pressures, at temperatures less than about 100° C., less than about 60° C., less than about 40° C., less than about 20° C., less than about 0° C., less than about −20° C., less than about −40° C., less than about −60° C., less than about −80° C., or any other suitable temperatures.

Freeze drying (lyophilization) may be carried out by freezing a solution of mirabegron at low temperatures and reducing the pressure as required for removing the solvent from the frozen solution of mirabegron. Temperatures that may be required to freeze the solution, depending on the solvent chosen to make the solution of mirabegron, may range from about −80° C. to about 0° C., or up to about 20° C. Temperatures that may be required to remove the solvent from the frozen solution may be less than about 20° C., less than about 0° C., less than about −20° C., less than about −40° C., less than about −60° C., less than about −80° C., or any other suitable temperatures.

Step c) involves the isolation of an amorphous form of mirabegron from the solution of step b). The compound obtained from step b) may be collected using techniques such as by scraping, or by shaking the container, or adding solvent to make slurry followed by filtration, or other techniques specific to the equipment used.

In embodiments of step c) the amorphous obtained from step b) may be optionally dried. Drying may be suitably carried out in a tray dryer, vacuum oven, Büchi® Rotavapor®, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. The drying may be carried out for any time period required for obtaining a desired quality, such as from about 15 minutes to 10 hours or longer.

In an aspect, the present invention provides solid dispersion of amorphous mirabegron together with one or more pharmaceutically acceptable carriers.

In an aspect, the amorphous solid dispersion of mirabegron and at least one pharmaceutically acceptable carrier according to the present invention has a ratio of at least one pharmaceutically acceptable carrier to the mirabegron at least about 1:2 to about 2:1 (w/w).

Figure 2:
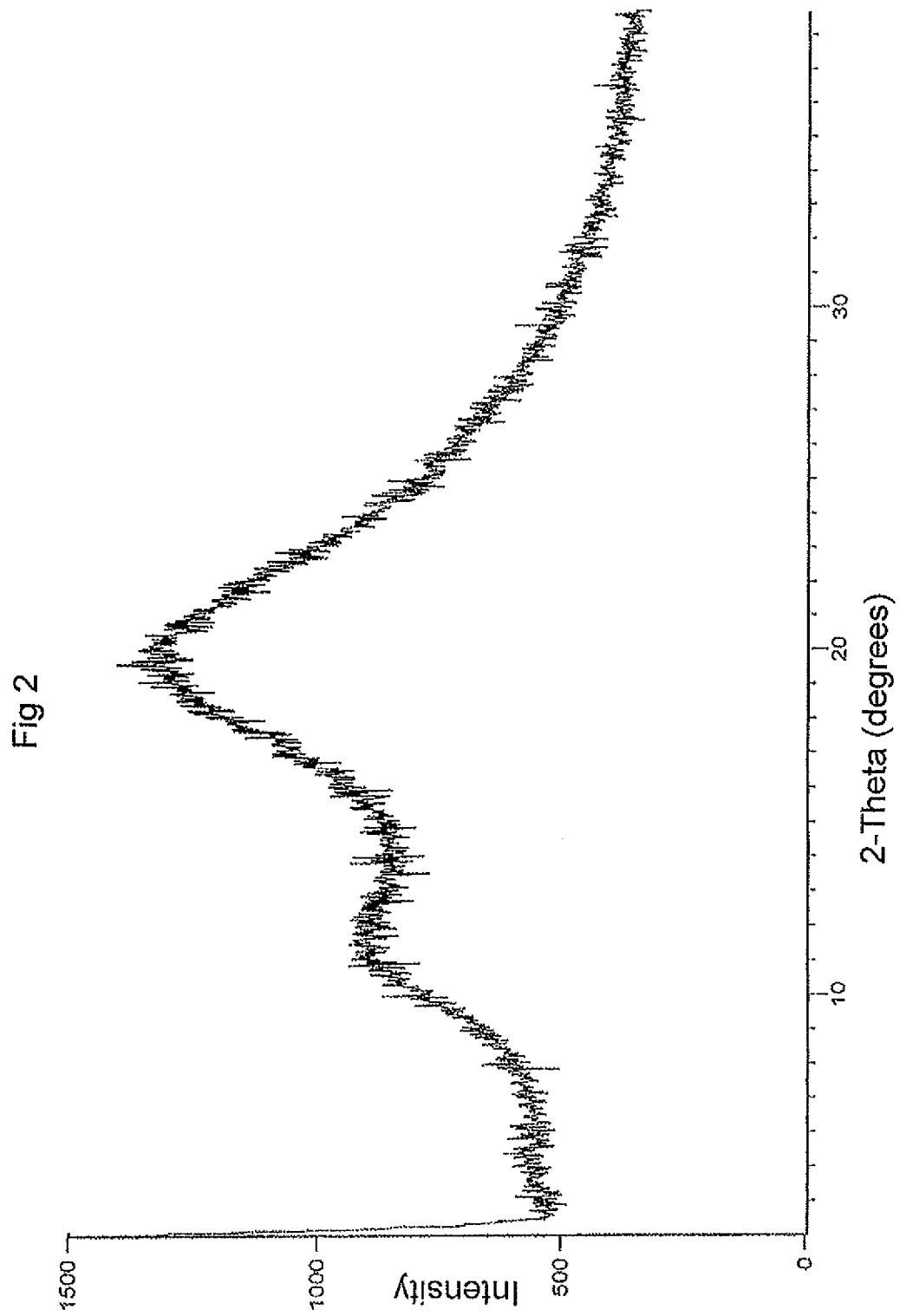
FIG. 2 is an illustration of a powder X-ray diffraction (PXRD) pattern of solid dispersion of amorphous mirabegron prepared according to Example 2.

In an aspect, the present invention provides solid dispersion of amorphous mirabegron together with one or more pharmaceutically acceptable carrier characterized by a powder X-ray diffraction (PXRD) pattern, substantially as illustrated by FIG. 2 or substantially as illustrated by FIG. 3.

In an aspect, the present invention provides a process for preparing a solid dispersion of amorphous mirabegron together with one or more pharmaceutically acceptable carriers, comprising:
 a) providing a solution or suspension of mirabegron in combination with one or more pharmaceutically acceptable carriers in a solvent or mixture of solvents;
 b) removing the solvent from the solution or suspension obtained in step a) or combining the solution obtained in step a), with an anti-solvent, and
 c) isolating solid dispersion of amorphous mirabegron together with one or more pharmaceutically acceptable carrier.

Step a) involves providing a solution or suspension of mirabegron in combination with one or more pharmaceutically acceptable carriers in a solvent or mixture of solvents.

In aspects, step a) may involve forming a solution of mirabegron together with one or more pharmaceutically acceptable carriers. In aspects, a carrier is one which enhances stability of the amorphous solid upon removal of the solvent.

Providing the solution in step a) includes:
i) solutions obtained from reaction mixtures in the final stage of processes for preparing the mirabegron, if desired, after addition of one or more pharmaceutically acceptable carriers; or
ii) dissolution of mirabegron in a suitable solvent, either alone or in combination with one or more pharmaceutically acceptable carriers.

In an aspect, the present invention provides a process for preparing a solid dispersion of amorphous mirabegron together with one or more pharmaceutically acceptable carriers, comprising:
a) blending mirabegron and at least one carrier selected form copovidone, povidone, methyl cellulose, hypromellose acetate succinate, polyethylene oxide, polyethylene glycol and one or more other pharmaceutically acceptable excipients;
b) heating the blend of step a) to form a molten slurry;
c) extruding the slurry of step b);
d) milling the extrudates of step c).

In an aspect, the present invention provides a process for preparing amorphous mirabegron or solid dispersion of amorphous mirabegron together with one or more pharmaceutically acceptable carriers, comprising:
a) providing a solution or suspension of mirabegron in combination with amorphous silica and one or more pharmaceutically acceptable carriers in a solvent or mixture of solvents;
b) spraying the mixture of step a) on a suitable substrate in a fluidized bed processor or top spray granulator;
c) drying the mass till desired loss on drying (LOD) is achieved.

Pharmaceutically acceptable carriers that may be used for the preparation of solid dispersions of mirabegron of the present invention include, but are not limited to: gelatines, ovalbumin, soybean proteins, gums, gum arabic, non-sucrose fatty acid esters, starches, modified starches, cellulose, cellulose derivative including microcrystalline cellulose, silicified microcrystalline cellulose, methylcellulose (MC), ethylcellulose (EC), hydroxy ethylcellulose (HEC), hydroxypropylcellulose (HPC), hydroxypropylmethylcellulose (HPMC), hypromellose acetate succinate (HPMC AS), hypromellose phthalate, polymers of carboxymethyl celluloses, polycarbophil, polyethylene glycol (PEG), propylene glycol derivatives, polyethylene oxides, polyoxyalkylene derivatives, polymethacrylates, copovidone, povidone, polyvinyl pyrrolidone (PVP, povidone), polyvinylpyrrolidones (homopolymers or copolymers), polyvinyl acetate (PVAc), PVP-vinylacetate-copolymer (PVP-VA), Kollidon VA 64 (a vinylpyrrolidone-vinyl acetate copolymer), sugars, lactose, fructose, polyvinyl alcohols, polyhydric alcohol, sorbitol, mannitol, maltitol, xylitol, saccharose, Isomalt, maltodextrin, dextrins, lactitol, cyclodextrins such as α-cyclodextrins, β-cyclodextrins, γ-cyclodextrins and hydroxylpropyl-β-cyclodextrins, sodium carboxymethylcellulose, sodium alginate, xantham gum, caavageenan, locust bean gum (*ceratonia*), chitosan, guar gum, cross-linked high amylase starch, and cross-linked polyacrylic acid (carbopol) or the like; or organic amines such as alkyl amines (primary, secondary, and tertiary), aromatic amines, alicyclic amines, cyclic amines, aralkyl amines, hydroxylamine or its derivatives, hydrazine or its derivatives, and guanidine or its derivatives. The use of mixtures of more than one of the pharmaceutical excipients to provide desired release profiles or for the enhancement of stability is within the scope of this invention. Also, all viscosity grades, molecular weights, commercially available products, their copolymers, and mixtures are all within the scope of this invention without limitation.

When the solution or suspension of mirabegron is prepared together with a pharmaceutically acceptable carrier, the order of charging different materials to the solution is not critical for obtaining the desired solid dispersion. A specific order may be preferred with respect to the equipment being used and will be easily determined by a person skilled in the art. Mirabegron or pharmaceutically acceptable carrier may be completely soluble in the solvent or they may form a suspension. In embodiments, mirabegron and the pharmaceutically acceptable carrier may be separately dissolved either in the same solvent or in different solvents, and then combined to form a mixture.

Suitable solvents that may be used in step a) include, but are not limited to, alcohol solvents; ketone solvents; halogenated hydrocarbon solvents; ester solvents; nitrile solvents; polar aprotic solvents; water; or mixtures thereof.

Suitable antioxidants include butylated hydroxytoluene (BHT), butyl hydroxy anisole (BHA), DL-α-tocopherol, propyl gallate, ascorbyl palmitate, malonic acid, fumaric acid and the like.

Suitable stabilizers include amorphous silica and the like.

Suitable substrate used in the fluid bed process or the top spray granulation process includes one or more of pharmaceutically acceptable carriers.

Suitable substrate used in the fluid bed process or the top spray granulation process is one or more of silicified microcrystalline cellulose, polyethylene glycol or polyethylene oxide (PEO) or mixture thereof.

The dissolution temperatures may range from 0° C. to about the reflux temperature of the solvent, depending on the solvent used for dissolution, as long as a clear solution of mirabegron is obtained without affecting its quality. The solution may optionally be treated with carbon, flux-calcined diatomaceous earth (Hyflow), or any other suitable material to remove color and/or to clarify the solution.

Optionally, the solution obtained above may be filtered to remove any insoluble particles. The solution may be filtered by passing through paper, glass fiber, or other membrane material, or a bed of a clarifying agent such as Celite® or Hyflow. Depending upon the equipment used and the concentration and temperature of the solution, the filtration apparatus may need to be preheated to avoid premature crystallization.

Step b) involves the removal of solvents from the solution obtained from step a). In an aspect, suitable techniques which may be used for the removal of the solvent include using a rotational distillation device such as a Büchi® Rotavapor®, spray drying, agitated thin film drying, freeze drying (lyophilization), atmospheric distillation, vacuum distillation, and the like, or any other suitable technique.

The solvent may be removed, optionally under reduced pressures, at temperatures less than about 100° C., less than about 60° C., less than about 40° C., less than about 20° C., less than about 0° C., less than about −20° C., less than about −40° C., less than about −60° C., less than about −80° C., or any other suitable temperatures.

Freeze drying (lyophilization) may be carried out by freezing a solution of mirabegron at low temperatures and reducing the pressure as required for removing the solvent from the frozen solution of mirabegron. Temperatures that may be required to freeze the solution, depending on the solvent chosen to make the solution of mirabegron, may range from about −80° C. to about 0° C., or up to about 20° C. Temperatures that may be required to remove the solvent from the frozen solution may be less than about 20° C., less than about 0° C., less than about −20° C., less than about −40° C., less than about −60° C., less than about −80° C., or any other suitable temperatures.

In another aspect, isolation may also be effected by combining the solution of step a) with a suitable anti-solvent optionally comprising one or more pharmaceutically acceptable carriers. Adding the solution obtained in step a) to the anti-solvent, or adding an anti-solvent to the solution obtained in step a), to effect the crystallization process are both within the scope of the present invention. Optionally, the addition may be carried out after concentrating the solution obtained in step a). Suitable anti-solvents that may be used include, but are not limited to: water; aliphatic or alicyclic hydrocarbon solvents; aromatic hydrocarbon solvents; ether solvents; or mixtures thereof.

In embodiments of step c) involves isolation of solid dispersion of amorphous mirabegron together with one or more pharmaceutically acceptable carriers from the solution of step a).

The compound obtained from step c) may be collected using techniques such as by scraping, or by shaking the container, or filtration, or adding solvent for making slurry followed by filtration, or other techniques specific to the equipment used. The product thus isolated may be optionally further dried to afford an amorphous form of mirabegron together with a pharmaceutically acceptable excipients. Drying may be suitably carried out in a tray dryer, vacuum oven, Büchi® Rotavapor®, air oven, fluidized bed dryer, spin flash dryer, flash dryer, or the like. The drying may be carried out at atmospheric pressure or under reduced pressures at temperatures of less than about 100° C., less than about 60° C., less than about 40° C., or any other suitable temperatures. The drying may be carried out for any time period required for obtaining a desired quality, such as from about 15 minutes to 10 hours or longer.

Examples of amorphous solid dispersions of mirabegron together with a pharmaceutically acceptable carrier obtained using the above process are characterized by their powder X-ray diffraction ("PXRD") patterns substantially as illustrated by FIGS. 2 and 3, respectively.

The solid dispersions differ from physical mixtures of amorphous mirabegron and one or more pharmaceutically acceptable carriers, so that individual particles of the components cannot be distinguished using techniques such as optical microscopy. In instances, the solid dispersions contain the components on a molecular level, such as in the nature of solid solutions.

In an aspect, the present invention provides a process for the preparation of α-form crystal of mirabegron comprising:
a) providing a solution of mirabegron in a solvent selected from methanol, ethanol, tetrahydrofuran, ethyl acetate, toluene or mixtures thereof;
b) cooling the solution obtained in step a), and
c) isolating α-form crystal of mirabegron.

In embodiments of step a) the solution of mirabegron can be obtained by dissolving mirabegron in a solvent selected from methanol, ethanol, tetrahydrofuran, ethyl acetate, toluene or mixtures thereof. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the solution obtained in step a) may be cooled to room temperature to produce α-form crystal of mirabegron. Preferably the solution may be cooled to 0-5° C. to produce α-form crystal of mirabegron. The cooling may be done slowly or rapidly. Preferably the cooling can be done slowly.

In embodiments of step c), α-form crystal of mirabegron can be isolated by the techniques known in the art such as filtration. In embodiments, α-form crystal of mirabegron can be optionally dried at the suitable temperature and pressure for a suitable time.

In an aspect, the present invention provides a process for the preparation of α-form crystal of mirabegron, comprising:
a) dissolving mirabegron in a mixture of methanol and water to provide a solution;
b) cooling the solution obtained in step a), and
c) isolating α-form crystal of mirabegron.

In embodiments of step a) the solution of mirabegron can be obtained by dissolving mirabegron in a mixture of methanol and water. In embodiments of step a) the ratio of methanol and water may be used in any suitable ratio. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the solution obtained in step a) may be cooled to about 0° C. to about 40° C. to produce α-form crystal of mirabegron. In embodiments, the solution may be cooled to about 10° C. to 30° C. The cooling may be done slowly or rapidly. Preferably the cooling can be done slowly.

In embodiments of step c), α-form crystal of mirabegron can be isolated by the techniques known in the art such as filtration. In embodiments, α-form crystal of mirabegron can be optionally dried at the suitable temperature and pressure for a suitable time.

In an aspect, the present invention provides a process for the preparation of α-form crystal of mirabegron, comprising:
a) providing a solution of mirabegron in a solvent selected from tetrahydrofuran, methanol, ethanol, acetone, acetonitrile, 1,4-dioxane, methyl isobutyl ketone, chlorobenzene or mixtures thereof;
b) adding an anti-solvent to the solution obtained from step a) selected from cyclohexane, methylcyclohexane, n-heptane, diisopropyl ether, methyl tertiary butyl ether, toluene, water, provided that when methanol is used as a solvent then anti-solvent is other than water; and
c) isolating α-form crystal of mirabegron.

Step a) involves the preparation of a solution of mirabegron by dissolving the mirabegron in a suitable inert solvent. The suitable solvent for making a solution can be selected from tetrahydrofuran, methanol, ethanol, acetone, acetonitrile, 1,4-dioxane, methyl isobutyl ketone, chlorobenzene or mixtures thereof. In embodiments, a solution of mirabegron can be prepared at any suitable temperatures, such as about 0° C. to about the reflux temperature of the solvent used. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the anti-solvent may be added to the solution obtained in step a). The anti-solvent can be added to the solution drop-wise, lot wise in one lot or more lots or rapidly. The anti-solvents may be selected from cyclohexane, methylcyclohexane, n-heptane, diisopropyl ether, methyl tertiary butyl ether, toluene, water. In embodiments, when methanol is used as a solvent in step a) then anti-solvent can be other than water.

In embodiments, slurry obtained by the precipitation comprising α-form crystal of mirabegron and inert solvent can be maintained at any suitable temperatures, such as about −10° C. to about 40° C., or about 0° C. to about 35° C. In embodiments, slurry comprising mirabegron can be maintained for about 30 minutes to about 10 hours, or longer.

In embodiments, the α-form crystal of mirabegron can be isolated using any techniques, such as decantation, filtration by gravity or suction, centrifugation, or the solvent can be evaporated from the mass to obtain the desired product, and optionally the solid can be washed with a solvent, such as an anti-solvent or the solvent, to reduce the amount of entrained impurities.

In embodiments, the α-form crystal of mirabegron that is isolated can be dried at suitable temperatures, and atmospheric or reduced pressures, for about 1-50 hours, or longer, using any types of drying equipment, such as a tray dryer, vacuum oven, air oven, fluidized bed dryer, spin flash dryer, flash dryer, and the like. Drying temperatures and times will be sufficient to achieve desired product purity.

In an aspect, the present invention provides a process for the preparation of α-form crystal of mirabegron comprising:
a) dissolving mirabegron in acetone to provide a solution;
b) adding the solution obtained from step a) to methylcyclohexane, and
c) isolating α-form crystal of mirabegron.

Step a) involves the preparation of solution of mirabegron by dissolving the mirabegron in acetone. In embodiments, a solution of mirabegron can be prepared at any suitable temperatures, such as about 0° C. to about the reflux temperature of the solvent used. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the solution obtained in step a) may be added to methylcyclohexane. The solution can be added to the methylcyclohexane drop-wise, lot wise in one or more lots or rapidly.

In embodiments, slurry obtained by the precipitation comprising α-form crystal of mirabegron and inert solvent can be maintained at any suitable temperatures, such as about −10° C. to about 40° C., or about 0° C. to about 35° C. In embodiments, slurry comprising mirabegron can be maintained for about 30 minutes to about 10 hours, or longer.

In embodiments, the α-form crystal of mirabegron can be isolated using any techniques, such as decantation, filtration by gravity or suction, centrifugation, or the solvent can be evaporated from the mass to obtain the desired product, and optionally the solid can be washed with a solvent, such as an anti-solvent or the solvent, to reduce the amount of entrained impurities.

In embodiments, the α-form crystal of mirabegron that is isolated can be dried at suitable temperatures, and atmospheric or reduced pressures, for about 1-50 hours, or longer, using any types of drying equipment, such as a tray dryer, vacuum oven, air oven, fluidized bed dryer, spin flash dryer, flash dryer, and the like. Drying temperatures and times will be sufficient to achieve desired product purity.

In an aspect, the present invention provides a process for the preparation of α-form crystal of mirabegron comprising:
a) providing a solution of mirabegron in a solvent or mixture of solvents, and
b) isolating the α-form crystal of mirabegron by the slow solvent evaporation.

In embodiments of step a), mirabegron can be dissolved in any suitable inert solvent. The suitable solvent for making a solution can be selected from the group of 2-butanol, ethanol, isopropyl alcohol, ethyl acetate, tetrahydrouran, chlorobenzene or any mixtures of two or more thereof. In embodiments, a solution of mirabegron can be prepared at any suitable temperatures, such as about 0° C. to about the reflux temperature of the solvent used. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments, the solution obtained from step a) may be kept for the evaporation of the solvent. In embodiment the solvent may be evaporated at the temperature about 10° C. to about 50° C. In embodiments, the solvent may be evaporated by keeping the solution in open at the room temperature till the evaporation of the solvent.

In embodiments, α-form crystal of mirabegron that is isolated can be dried at suitable temperatures, and atmospheric or reduced pressures, for about 1-50 hours, or longer, using any types of drying equipment, such as a tray dryer, vacuum oven, air oven, fluidized bed dryer, spin flash dryer, flash dryer, and the like. Drying temperatures and times will be sufficient to achieve desired product purity.

In a further aspect α-form crystal of mirabegron can be prepared by slurring the crude mirabegron in a suitable solvent. The crude mirabegron can be crystalline, mixture of crystalline and amorphous, solvate or hydrate.

In an aspect, the present invention provides a process for the preparation of β-form crystal of mirabegron comprising:
a) dissolving mirabegron in methyl isobutyl ketone to provide a solution;
b) cooling the solution obtained in step a), and
c) isolating β-form crystal of mirabegron.

In embodiments of step a) the solution of mirabegron can be obtained by dissolving the mirabegron in methyl isobutyl ketone. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the solution obtained in step a) may be cooled to 0 to 5° C. to produce the β-form crystal of mirabegron. The cooling may be done slowly or rapidly. Preferably the cooling can be slowly.

In embodiments of step c), the β-form crystal of mirabegron can be isolated by the techniques known in the art such as filtration. In embodiments, the β-form crystal of mirabegron can be optionally dried at the suitable temperature and pressure for a suitable time.

In an aspect, the present invention provides a process for the preparation of β-form crystal of mirabegron comprising:
  a) providing a solution of mirabegron in a solvent selected from tetrahydrofuran, formamide, N,N-dimethylformamide, N,N-dimethylacetamide, 2-methoxyethanol, morpholine or mixtures thereof;
  b) adding the solution obtained from step a) to an anti-solvent selected from methylcyclohexane, n-heptane, toluene and water, and
  c) isolating β-form crystal of mirabegron.

Step a) involves the preparation of solution of mirabegron by dissolving the mirabegron in a suitable inert solvent. The suitable solvent for making a solution can be selected from tetrahydrofuran, formamide, N,N-dimethylformamide, N,N-dimethylacetamide, 2-methoxyethanol, morpholine or mixtures thereof. In embodiments, a solution of mirabegron can be prepared at any suitable temperatures, such as about 0° C. to about the reflux temperature of the solvent used. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the solution obtained in step a) may be added to a suitable anti-solvent. The solution can be added to the anti-solvent drop-wise, lot wise in one or more lots or rapidly. The anti-solvents may be selected from the group of methylcyclohexane, n-heptane, toluene and water.

In embodiments, slurry obtained by the precipitation comprising β-form crystal of mirabegron and inert solvent can be maintained at any suitable temperatures, such as about −10° C. to about 40° C., or about 0° C. to about 35° C. In embodiments, slurry comprising mirabegron can be maintained for about 30 minutes to about 10 hours, or longer.

In embodiments, the β-form crystal of mirabegron can be isolated using any techniques, such as decantation, filtration by gravity or suction, centrifugation, or the solvent can be evaporated from the mass to obtain the desired product, and optionally the solid can be washed with a solvent, such as an anti-solvent or the solvent, to reduce the amount of entrained impurities.

In embodiments, the β-form crystal of mirabegron that is isolated can be dried at suitable temperatures, and atmospheric or reduced pressures, for about 1-50 hours, or longer, using any types of drying equipment, such as a tray dryer, vacuum oven, air oven, fluidized bed dryer, spin flash dryer, flash dryer, and the like. Drying temperatures and times will be sufficient to achieve desired product purity.

In an aspect, the present invention provides a process for the preparation of β-form crystal of mirabegron comprising:
  a) providing a solution of mirabegron in a solvent selected from dimethylsulfoxide, morpholine, ethyl acetate, or mixtures thereof;
  b) adding an anti-solvent selected from the group of n-heptane and water to the solution obtained from step a), and
  c) isolating β-form crystal of mirabegron.

Step a) involves the preparation of a solution of mirabegron by dissolving the mirabegron in a suitable inert solvent. The suitable solvent for making a solution can be selected from dimethylsulfoxide, morpholine, ethyl acetate, or mixture of one or more thereof. In embodiments, a solution of mirabegron can be prepared at any suitable temperatures, such as about 0° C. to about the reflux temperature of the solvent used. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) the anti-solvent may be added to the solution obtained in step a). The anti-solvent can be added to the solution drop-wise, lot wise in one or more lots or rapidly. The anti-solvents may be selected from n-heptane and water.

In embodiments, slurry obtained by the precipitation comprising β-form crystal of mirabegron and inert solvent can be maintained at any suitable temperatures, such as about −10° C. to about 40° C., or about 0° C. to about 35° C. In embodiments, slurry comprising mirabegron can be maintained for about 30 minutes to about 10 hours, or longer.

In embodiments, the β-form crystal of mirabegron can be isolated using any techniques, such as decantation, filtration by gravity or suction, centrifugation, or the solvent can be evaporated from the mass to obtain the desired product, and optionally the solid can be washed with a solvent, such as an anti-solvent or the solvent, to reduce the amount of entrained impurities.

In embodiments, β-form crystal of mirabegron that is isolated can be dried at suitable temperatures, and atmospheric or reduced pressures, for about 1-50 hours, or longer, using any types of drying equipment, such as a tray dryer, vacuum oven, air oven, fluidized bed dryer, spin flash dryer, flash dryer, and the like. Drying temperatures and times will be sufficient to achieve desired product purity.

In an aspect, the present invention provides a process for the preparation of β-form crystal of mirabegron comprising:
  a) dissolving mirabegron in methanol to provide a solution;
  b) adding water to the solution obtained in step a)
  c) isolating β-form crystal of mirabegron.

In embodiments of step a) the solution of mirabegron can be obtained by dissolving the mirabegron in methanol. Stirring and heating may be used to reduce the time required for the dissolution process.

In embodiments, a solution of mirabegron may be filtered to make it clear, free of unwanted particles. In embodiments, the obtained solution may be optionally treated with an adsorbent material, such as carbon and/or hydrose, to remove colored components, etc., before filtration.

In embodiments of step b) water can be added to the solution obtained in step a). The addition of water to the solution can be drop-wise, lot-wise in one lot or more lots.

In embodiments of step c), the β-form crystal of mirabegron can be isolated by the techniques known in the art such as filtration. In embodiments, the β-form crystal of mirabegron can be optionally dried at the suitable temperature and pressure for a suitable time.

In embodiments, amorphous mirabegron, solid dispersion of amorphous mirabegron, α-form crystal of mirabegron and β-form crystal of mirabegron obtained from the present invention may be optionally milled to get desired particle sizes. Milling or micronization may be performed before drying, or after the completion of drying of the product. Techniques that may be used for particle size reduction include, without limitation, ball, roller and hammer mills, and jet mills.

In an aspect of the invention mirabegron obtained according to certain processes of the present invention has a particle size distribution wherein: mean particle size is less than about 200 μm or less than about 100 μm; d (0.5) is less than about 200 μm or less than about 25 μm; and d (0.9) is less than about 500 μm or less than about 50 μm.

In an aspect of the invention, mirabegron prepared according to the precesses of the present invention can be substantially pure having a chemical purity greater than about 99%, or greater than about 99.5%, or greater than about 99.9%, by weight, as determined using high performance liquid chromatography (HPLC). Mirabegron produced by a method of present invention can be chemically pure mirabegron having purity greater than about 99.5% and containing no single impurity in amounts greater than about 0.15%, by HPLC. Mirabegron produced by the methods of present invention can be chemically pure mirabegron having purity greater than about 99.8% and containing no single impurity in amounts greater than about 0.1%, by HPLC.

In an aspect of the invention, mirabegron obtained by the methods of the present invention can be further purified by using techniques known in the art to enhance its chemical purity and chiral purity.

Mirabegron which is used as a starting material in the present invention can be in any physical form such as crystalline, amorphous, mixture of crystalline and amorphous, solvates, hydrates etc., Mirabegron that may be used as the input for the processes of the present invention may be obtained by any process including the processes described in the art and optionally can be purified using any method known in the art to enhance its chemical purity. For example mirabegron may be prepared by the processes described in U.S. Pat. No. 6,346,532 or U.S. Pat. No. 7,342,117.

In an aspect, present invention also provides a pharmaceutical composition comprising amorphous form of mirabegron along with one or more pharmaceutically acceptable carriers, excipients, or diluents.

In an aspect, the present invention also provides pharmaceutical composition comprising solid dispersions of amorphous mirabegron together with one or more pharmaceutically acceptable excipients.

In an aspect, the present invention also provides pharmaceutical composition comprising the α-form crystal of mirabegron obtained according to the any of the processes described in this application.

A solid dispersion of mirabegron together with one or more pharmaceutically acceptable excipients of the present invention may be further formulated as: solid oral dosage forms such as, but not limited to: powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the forms of immediate release, delayed release or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using techniques such as direct blending, dry granulation, wet granulation, and extrusion and spheronization. Compositions may be presented as uncoated, film coated, sugar coated, powder coated, enteric coated, and modified release coated. Compositions of the present invention may further comprise one or more pharmaceutically acceptable excipients.

Pharmaceutically acceptable excipients that are useful in the present invention include, but are not limited to: diluents such as starches, pregelatinized starches, lactose, powdered celluloses, microcrystalline celluloses, dicalcium phosphate, tricalcium phosphate, mannitol, polysorbate, sorbitol, sugar or the like; binders such as acacia, guar gum, tragacanth, gelatin, polyvinylpyrrolidones, hydroxypropyl celluloses, hydroxypropyl methylcelluloses, pregelatinized starches or the like; disintegrants such as starches, sodium starch glycolate, pregelatinized starches, crospovidones, croscarmellose sodium, colloidal silicon dioxide or the like; lubricants such as stearic acid, magnesium stearate, zinc stearate or the like; glidants such as colloidal silicon dioxide or the like; solubility or wetting enhancers such as anionic or cationic or neutral surfactants; complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes or the like. Other pharmaceutically acceptable excipients that are of use include but are not limited to film formers, plasticizers, colorants, flavoring agents, sweeteners, viscosity enhancers, preservatives, antioxidants, or the like.

The new polymorphic forms of mirabegron of the present invention are useful for the treatment of a disease associated with overactive bladder.

In as aspect, the present invention provides a method for the treatment of a disease associated with overactive bladder in a patient comprising administering a therapeutically effective amount of the α-form crystal of mirabegron obtained according to the present invention together with at least one pharmaceutically acceptable carrier.

In as aspect, the present invention provides a method for the treatment of a disease associated with overactive bladder in a patient comprising administering a therapeutically effective amount of amorphous solid dispersion of mirabegron together with at least one pharmaceutically acceptable carrier.

DEFINITIONS

The following definitions are used in connection with the present invention unless the context indicates otherwise. The term "amorphous" refers to a solid lacking any long-range translational orientation symmetry that characterizes crystalline structures although; it may have short range molecular order similar to a crystalline solid. The term "antisolvent" refers to a liquid that, when combined with a solution of mirabegron, reduces solubility of the mirabegron in the solution, causing crystallization or precipitation in some instances spontaneously, and in other instances with additional steps, such as seeding, cooling, scratching and/or concentrating. Celite® is flux-calcined diatomaceous earth. Celite® is a registered trademark of World Minerals Inc. Hyflow is flux-calcined diatomaceous earth treated with sodium carbonate. Hyflo Super Cel™ is a registered trademark of the Manville Corp. Polymorphs are different solids sharing the same molecular formula, yet having distinct physical properties when compared to other polymorphs of the same formula. Povidone K-90 is poly(1-vinyl-2-pyrrolidinone) with an average M.W. of 360,000.

An "alcohol solvent" is an organic solvent containing a carbon bound to a hydroxyl group. "Alcoholic solvents" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, $C_{1-6}$alcohols, or the like.

An "aliphatic or alicyclic hydrocarbon solvent" refers to a liquid, non-aromatic, hydrocarbon, which may be linear, branched, or cyclic. It is capable of dissolving a solute to form a uniformly dispersed solution. Examples of a hydrocarbon solvents include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$aliphatic hydrocarbons, petroleum ethers, or mixtures thereof.

"Aromatic hydrocarbon solvent" refers to a liquid, unsaturated, cyclic, hydrocarbon containing one or more rings which has at least one 6-carbon ring containing three double bonds. It is capable of dissolving a solute to form a uniformly dispersed solution. Examples of aromatic hydrocarbon solvents include, but are not limited to, benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$aromatic hydrocarbons, or mixtures thereof.

An "ester solvent" is an organic solvent containing a carboxyl group —(C=O)—O— bonded to two other carbon atoms. "Ester solvents" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, $C_{3-6}$esters, or the like.

A "halogenated hydrocarbon solvent" is an organic solvent containing a carbon bound to a halogen. "Halogenated hydrocarbon solvents" include, but are not limited to, dichloromethane, 1,2-dichloroethane, trichloroethylene, perchloroethylene, 1,1,1-trichloroethane, 1,1,2-trichloroethane, chloroform, carbon tetrachloride, or the like.

A "ketone solvent" is an organic solvent containing a carbonyl group —(C=O)— bonded to two other carbon atoms. "Ketone solvents" include, but are not limited to, acetone, ethyl methyl ketone, diethyl ketone, methyl isobutyl ketone, $C_{3-6}$ketones, 4-methyl-pentane-2-one or the like.

A "nitrile solvent" is an organic solvent containing a cyano —(C≡N) bonded to another carbon atom. "Nitrile solvents" include, but are not limited to, acetonitrile, propionitrile, $C_{2-6}$nitriles, or the like.

A "polar aprotic solvent" has a dielectric constant greater than 15 and is at least one selected from the group consisting of amide-based organic solvents, such as N,N-dimethylformamide (DMF), N,N-dimethylacetamide (DMA), N-methylpyrrolidone (NMP), formamide, acetamide, propanamide, hexamethyl phosphoramide (HMPA), and hexamethyl phosphorus triamide (HMPT); nitro-based organic solvents, such as nitromethane, nitroethane, nitropropane, and nitrobenzene; pyridine-based organic solvents, such as pyridine and picoline; sulfone-based solvents, such as dimethylsulfone, diethylsulfone, diisopropylsulfone, 2-methylsulfolane, 3-methylsulfolane, 2,4-dimethylsulfolane, 3,4-dimethysulfolane, 3-sulfolene, and sulfolane; and sulfoxide-based solvents such as dimethylsulfoxide (DMSO).

An "ether solvent" is an organic solvent containing an oxygen atom —O— bonded to two other carbon atoms. "Ether solvents" include, but are not limited to, diethyl ether, diisopropyl ether, methyl t-butyl ether, glyme, diglyme, tetrahydrofuran, 2-methyltetrahydrofuran, 1,4-dioxane, dibutyl ether, dimethylfuran, 2-methoxyethanol, 2-ethoxyethanol, anisole, $C_{2-6}$ethers, or the like.

An "excipient" is any useful pharmaceutically acceptable additive in the context of the present invention which comprises diluents, binders, disintegrants, lubricants, surfactants, antioxidant, stabilizers, glidants, coating agents, and the like.

"Effective amount" or "therapeutically effective amount" denotes an amount of an active ingredient that, when administered to a subject for treating a disease associated with overactive bladder, produces an intended therapeutic benefit in a subject.

Certain specific aspects and embodiments of the present invention will be explained in more detail with reference to the following examples, which are provided for purposes of illustration only and should not be construed as limiting the scope of the present invention in any manner.

EXAMPLES

All PXRD data reported herein are obtained using a Bruker AXS D8 Advance Powder X-ray Diffractometer or a PANalytical X-ray Diffractometer, using copper Kα radiation.

Example 1

Preparation of Amorphous Form of Mirabegron

Mirabegron (1.0 g) and acetone (160 mL) were charged in to a round-bottom flask at 25-35° C. The contents were heated to 40-53° C. and stirred to dissolve mirabegron completely. The resulting solution was evaporated completely in Büchi® Rotavapor® at 40-45° C. under reduced pressure to afford 800 mg of the title compound. PXRD pattern is shown as FIG. 1.

Example 2

Preparation of a Solid Dispersion of Amorphous Mirabegron with Povidone

Mirabegron (500 mg) and 4-methylpentane-2-one (35.0 mL) were charged in to a round bottom flask at 25-35° C. The contents were heated to 70-75° C. and stirred to dissolve mirabegron completely. Povidone K-90 (500 mg) and n-heptane (90 mL) were charged in to another round bottom flask at 25-35° C. and stirred for 5-10 minutes. The reaction mixture was cooled to 5 to 10° C. Above obtained solution of mirabegron in 4-methylpentane-2-one was charged to the mixture at 5-10° C. and the reaction mixture was stirred for 10-15 minutes. The obtained solid was collected by filtration, washed with n-heptane (5 mL) to afford 1.10 g of the title material. PXRD pattern is shown as FIG. 2.

Example 3

Preparation of a Solid Dispersion of Amorphous Mirabegron with Povidone

Mirabegron (1.0 g) and acetone (160 mL) were charged in to a round bottom flask at 25-35° C. The contents were heated to 50-53° C. and stirred to dissolve mirabegron completely. The resulting solution was evaporated completely in Büchi® Rotavapor® at 40-45° C. under reduced pressure. Dichloromethane (180 mL) was charged to the reaction mass and stirred at 38-39° C. Povidone K-90 (1.0 g) and dichloromethane (50 mL) were charged in to another round bottom flask at 25-35° C. The contents were heated to 35-38° C. and stirred to dissolve povidone-K-90 completely. The resultant solution of povidone-K-90 in dichloromethane was charged to the above obtained solution of mirabegron in dichloromethane at 30-35° C. The reaction mixture was stirred at 30-35° C. for 10-15 minutes. The solvent from the mixture was evaporated under reduced pressure at 35-40° C. to afford 1.82 g of the title material. PXRD pattern is shown as FIG. 3.

Example 4

Preparation of a Solid Dispersion of Amorphous Mirabegron with Povidone (1:1)

Mirabegron (7.0 g), Povidone K-90 (7.0 g) and methanol (700 mL) were charged in to a round-bottom flask at 27° C. The contents were stirred at 27° C. to obtain clear solution. The resulting solution was evaporated completely in Büchi® Rotavapor® at 50-55° C. under reduced pressure to afford 12.0 g of the title compound. PXRD pattern is shown as FIG. 3.

Example 5

Preparation of a Solid Dispersion of Amorphous Mirabegron with Povidone (2:1)

Mirabegron (9.0 g), Povidone K-90 (4.5 g) and methanol (700 mL) were charged in to a round-bottom flask at 27° C. The contents were stirred at 27° C. to obtain clear solution. The resulting solution was evaporated completely in Büchi® Rotavapor® at 50-55° C. under reduced pressure to afford 11.5 g of the title compound. PXRD pattern is shown as FIG. 3.

Example 6

Preparation of β-Form Crystal of Mirabegron

Mirabegron (500 mg) and tetrahydrofuran (20 mL) were charged into a round bottom flask at 27° C. The obtained suspension was stirred and heated to 40° C. to get a clear solution. The clear solution was added to the methylcyclohexane (40 mL) at 10° C. and stirred for 15 minutes at the same temperature. The precipitated solid was collected by filtration and washed with methylcyclohexane (5 mL) and dried to afford 180 mg of the title compound.

Examples 7-13

Preparation of β-Form Crystal of Mirabegron

Mirabegron (500 mg) and a solvent were charged into a round bottom flask. The mixture was stirred to obtain a clear solution. If required, the mixture was heated to obtain a clear solution. The clear solution was added to an anti-solvent. The mass was maintained to precipitate the solid (if required, using cooling) and the formed solid was collected by filtration, washed with a small quantity of anti-solvent, and then dried to produce β-form crystal of mirabegron. The following examples illustrate the preparation of β-form crystal of mirabegron following this procedure.

| Example | Solvent (mL) | Anti-solvent (mL) | Yield (mg) |
|---|---|---|---|
| 7 | Tetrahydrofuran (20) | n-Heptane (40) | 280 |
| 8 | N,N-dimethylformamide (10) | water (30) | 280 |
| 9 | Formamide (20) | water (40) | 310 |
| 10 | N,N-dimethylacetamide (10) | water (30) | 380 |
| 11 | Tetrahydrofuran (20) | Toluene (40) | 310 |
| 12 | 2-methoxyethanol (20) | water (40) | 380 |
| 13 | Morpholine (10) | n-Heptane (30) | 410 |

Examples 14-17

Preparation of β-Form Crystal of Mirabegron

Mirabegron (500 mg) and a solvent were charged into a round bottom flask. The mixture was stirred to obtain a clear solution. If required, the mixture was heated to obtain a clear solution. The clear solution was cooled if required. An anti-solvent was added to the solution. The mass was maintained to precipitate a solid (if required, using cooling) and the formed solid was collected by filtration, washed with a small quantity of anti-solvent and then dried to produce β-form crystal of mirabegron. The following examples illustrate the preparation of β-form crystal of mirabegron, following this procedure.

| Example | Solvent (mL) | Anti-solvent (mL) | Yield (mg) |
|---|---|---|---|
| 14 | Methanol (10) | water (40) | 410 |
| 15 | Dimethylsulfoxide (3) | water (15) | 420 |
| 16 | Morpholine (0.5) and N-methylpyrolidine (15) | water (50) | 380 |
| 17 | Ethyl acetate (120) and water (0.5) | n-Heptane (240) | 410 |

Examples 18

Preparation of β-Form Crystal of Mirabegron

Mirabegron (1.0 g) and Methyl isobutyl ketone (230 mL) were charged into a round bottom flask at 27° C. The obtained suspension was stirred and heated to 70° C. to get a clear solution. The solution was cooled to 27° C. under stirring and further cooled to 5° C. and stirred for 10 minutes at 5° C. The precipitated solid compound was filtered and washed with methyl isobutyl ketone (5 mL) and dried under suction for 5 minutes to obtain 410 mg of the title compound.

Examples 19-34

Preparation of α-Form Crystal of Mirabegron

Mirabegron (500 mg) and a solvent were charged into a round bottom flask. The mixture was stirred to obtain a clear solution. If required, the mixture was heated to obtain a clear solution. An anti-solvent was added to the solution. The mass was maintained to precipitate the solid (if required, using cooling) and the formed solid was collected by filtration, washed with a small quantity of anti-solvent, and then dried to produce α-form crystal of mirabegron. The following examples illustrate the preparation of α-form crystal of mirabegron following this procedure.

| Example | Solvent (mL) | Anti-solvent (mL) | Yield (mg) |
|---|---|---|---|
| 19 | Tetrahydrofuran (20) | Methylcyclohexane (40) | 360 |
| 20 | Tetrahydrofuran (20) | Cyclohexane (40) | 400 |
| 21 | Tetrahydrofuran (20) | Water (40) | 310 |
| 22 | Tetrahydrofuran (20) | Diisopropyl ether (40) | 320 |
| 23 | Tetrahydrofuran (20) | Toluene (40) | 150 |
| 24 | Methanol (10) | Methyl tertiary butyl ether (40) | 410 |
| 25 | Methanol (10) | Diisopropyl ether (40) | 320 |
| 26 | Ethanol (0.5) and acetone (70) | Methylcyclohexane (150) | 480 |
| 27 | Acetonitrile (0.5) and Methylisobutylketone (50) | Methylcyclohexane (150) | 380 |
| 28 | Acetonitrile (0.5) and Tetrahydrofuran (60) | n-Heptane (120) | 280 |
| 29 | 1,4-Dioxane (0.5) and Acetone (70) | Methylcyclohexane (150) | 380 |
| 30 | Chlorobenzene (0.5) and Methyl isobutyl ketone (120) | Methylcyclohexane (140) | 380 |
| 31 | Chlorobenzene (0.5) and Tetrahydrofuran (60) | n-Heptane (120) | 280 |
| 32 | Methanol (0.2) and Methyl isobutyl ketone (70) | n-Heptane (150) | 480 |
| 33 | Methanol (0.2) and Tetrahydrofuran (60) | Methylcyclohexane (120) | 410 |
| 34 | Water (0.5) and Methyl isobutyl ketone (120) | Cyclohexane (240) | 410 |

Examples 35-40

Preparation of α-Form Crystal of Mirabegron

Mirabegron (100 mg) and a solvent were charged into a round bottom flask. The mixture was stirred to obtain a clear solution. If required, the mixture was heated to obtain a clear solution. The clear solution was kept for slow evaporation at room temperature to produce α-form crystal of mirabegron. The following examples illustrate the preparation of α-form crystal of mirabegron following this procedure.

| Example | Solvent (mL) | Yield (mg) |
|---|---|---|
| 35 | 2-Butanol (16) | 88 |
| 36 | Ethanol (12) | 92 |
| 37 | Isopropyl alcohol (20) | 80 |
| 38 | Chlorobenzene (15) | 90 |
| 39 | Ethyl acetate (20 mL) | 80 |
| 40 | Tetrahydrofuran (5) | 90 |

Examples 41

Preparation of α-Form Crystal of Mirabegron

Mirabegron (500 mg) and acetone (15 mL) were charged into a round bottom flask at 27° C. The obtained suspension was stirred and heated to 50° C. to get a clear solution. The clear solution was added to methylcyclohexane (50 mL) at 5° C. and stirred for 15 minutes at the same temperature. The solution was kept for the slow evaporation of solvent at room temperature. The obtained solid was collected by filtration and washed with methylcyclohexane (5 mL). The material was dried under suction at 27° C. for 5 minutes to afford 280 mg of the title compound.

Examples 42

Preparation of α-Form Crystal of Mirabegron

Mirabegron (1.0 g) and tetrahydrofuran (80 mL) were charged into a round bottom flask at 27° C. The obtained suspension was stirred and heated to 70° C. to get a clear solution. The solution was cooled to 27° C. under stirring in 25 minutes and further cooled to 5° C. and stirred for 10 minutes at 5° C. The precipitated solid compound was filtered and washed with tetrahydrofuran (5 mL) and dried under suction for 5 minutes to obtain 410 mg of the title compound.

Examples 43

Preparation of α-Form Crystal of Mirabegron

Mirabegron (500 mg) and ethyl acetate (140 mL) were charged into a round bottom flask at 27° C. The obtained suspension was stirred and heated to 65° C. to get a clear solution. The solution was cooled to 27° C. under stirring in 25 minutes and further cooled to 5° C. and stirred for 10 minutes at 5° C. The precipitated solid compound was filtered and washed with ethyl acetate (5 mL) and dried under suction for 5 minutes to obtain 218 mg of the title compound.

Examples 44

Preparation of α-Form Crystal of Mirabegron

Mirabegron (500 mg) and toluene (100 mL) were charged into a round bottom flask at 27° C. The obtained suspension was stirred and heated to 110° C. to get a clear solution. The solution was cooled to 27° C. under stirring in 30 minutes and further cooled to 5° C. and stirred for 10 minutes at 5° C. The precipitated solid compound was filtered and washed with toluene (5 mL) and dried under suction for 5 minutes to obtain 470 mg of the title compound Examples 45

Preparation of α-Form Crystal of Mirabegron

Mirabegron (3 g), methanol (12 mL) and water (12 mL) were charged into a round bottom flask at 26° C. The obtained suspension was stirred and heated to 62° C. to get a clear solution. The clear solution was cooled to 27° C. and stirred for 3 hours at the same temperature. The precipitated solid was collected by filtration and washed with water (5 mL) and dried under vacuum at 70° C. for 4 hours. Yield: 2.0 g.

Examples 46

Preparation of α-Form Crystal of Mirabegron

Mirabegron (2.0 g) and methanol (6 mL) were charged into a round bottom flask at 27° C. The obtained suspension was stirred and heated to 63° C. to get a clear solution. The solution was cooled to 27° C. under stirring in 1 hour and stirred for 2 hours and 30 30 minutes at 27° C. The precipitated solid compound was filtered and dried under vacuum at 50° C. for 2 hours to obtain 1.1 g of the title compound.

Examples 47

Preparation of α-Form Crystal of Mirabegron

Mirabegron (2.0 g) and ethanol (20 mL) were charged into a round bottom flask at 27° C. The obtained suspension was stirred and heated to 75° C. to get a clear solution. The solution was cooled to 27° C. under stirring in 1 hour and stirred for 2 hours at 27° C. The precipitated solid compound was filtered and dried under vacuum at 50° C. for 2 hours and 30 minutes to obtain 1.2 g of the title compound.

Examples 48-52

Amorphous Mirabegron Solid Dispersion

To a solution of Mirabegron in a suitable solvent, an excipient and optionally an antioxidant was added and stirred for complete dissolution. This solution was heated to obtain a clear solution and filtered if required. The solution was later spray dried under following conditions to obtain the title compound.
In-let temperature: 65° C.
Aspiration: 70-75%
Pump rate: 20-30%
Out-let temperature: 35-40° C.
The following examples (Ex.) illustrate the preparation of amorphous Mirabegron solid dispersion, following this procedure.

| Ex. | Mirabegron (g) | Solvent (mL) | Excipient (g) | Antioxidant (g) | Yield | Purity by HPLC | PXRD |
|---|---|---|---|---|---|---|---|
| 48 | 20 | Methanol (300) | HPC (20) | BHT (0.300) | 14.0 g | 99.82% | Amorphous |
| 49 | 13 | Methanol (500) | HPC (26) | — | 18.4 g | 99.76% | Amorphous |
| 50 | 25 | Methanol (600) | HPC (25) | — | 31.2 g | — | Amorphous |
| 51 | 25 | Methanol (500) | Copovidone (25) | — | 22.0 g | 99.87% | Amorphous |
| 52 | 25 | Methanol (500) | Copovidone (25 g) | BHT (0.375) | 31.0 g | — | Amorphous |

Examples 53-57

Preparation of Solid Dispersion of Amorphous Mirabegron Using Hot Melt Extrusion Accurately weighed quantity of Mirabegron, pharmaceutically acceptable carrier were sifted and blended in double cone blender. The blend was extruded on twin screw extruder (16M Thermo Scientific) at certain temperature. The extrudates were milled using Quadra co-mill and sifted. The following examples 49-55 illustrate the preparation of the amorphous mirabegron following the hot-melt extrusion technique.

| | Composition | | | | | | |
|---|---|---|---|---|---|---|---|
| Ingredients (%) | 53 | 54 | 55 | 56 | 57 | 58 | 59 |
| Mirabegron | 50 | 40 | 50 | 40 | 75 | 50 | 50 |
| Copovidone (Kolidone VA64) | 50 | | | | | | |
| Methyl cellulose | | 40 | 50 | | | | |
| Hypromellose acetate succinate (HPMC AS) | | | | 60 | 25 | | |
| Povidone K 30 (PVP K30) | | | | | | 50 | |
| Hydroxy propyl cellulose (HPC) powder grade | | | | | | | 50 |
| Colloidal silicon dioxide (Aerosil 200) | | | 10 | | | | |
| DL-α-tocopherol | | | | | | | q.s. |

Examples 60-63

Preparation of Solid Dispersion of Amorphous Mirabegron Using Fluidized Bed Processor Accurately weighed quantity of Mirabegron, amorphous silica (Syloid), and a suitable substrate was sifted. Mirabegron, amorphous silica (Syloid), optionally the butylated hydroxytoluene (BHT) was dissolved in a solvent. The above solvent mixture was sprayed on suitable substrate pre-loaded in a fluidized bed processor. The mixture was granulated and the mass was dried till desired LOD is achieved. The granules were sifted and further processed into a suitable formulation. The following examples 60-62 illustrate the preparation of the amorphous mirabegron using Fluidized bed processor.

| Ingredients | | Composition | | | |
|---|---|---|---|---|---|
| (Qty in mg) | Category | 60 | 61 | 62 | 63 |
| Mirabegron | API | 25 | 25 | 50 | 50 |
| Amorphous silica (Syloid) | Stabilizer | 12.5 | 12.5 | 25 | — |
| Hydroxypropyl cellulose | Binder | 7.5 | 7.5 | — | |
| Copovidone (Kolidone VA64) | Binder | — | — | 7.5 | 100 |
| Butylated hydroxytoluene (BHT) | antioxidant | 0.37 | — | — | 0.37 |
| Substrate | Substrate | 202.5 | 202.5 | 165.5 | 107.0 |
| Methanol | Solvent | q.s. | q.s. | q.s. | q.s. |

Examples 64-67

Preparation of Solid Dispersion of Amorphous Mirabegron Using Top Spray Granulator Example 60-63 were reproduced using a top spray granulator.

The invention claimed is:

1. An amorphous solid dispersion of mirabegron together with one or more pharmaceutically acceptable carriers and optionally one or more pharmaceutically acceptable antioxidant.

2. The amorphous solid dispersion of mirabegron of claim 1, wherein one or more pharmaceutically acceptable carrier is selected from gelatines, ovalbumin, soybean proteins, gum arabic, non-sucrose fatty acid esters, starches, modified starches, cellulose, methylcellulose (MC), ethylcellulose (EC), hydroxy ethylcellulose (HEC), hydroxypropylcellulose (HPC), hydroxypropylmethylcellulose (HPMC), hypromellose acetate succinate (HPMC AS), polycarbophil, polyethylene glycol (PEG), polyethylene oxides, polyoxyalkylene derivatives, polymethacrylates, polyvinyl pyrrolidone (PVP, povidone), polyvinyl acetate (PVAc), PVP-vinylacetate-copolymer (PVP-VA), Kollidon VA 64 (a vinylpyrrolidone-vinyl acetate copolymer), lactose, sorbitol, mannitol, maltitol, saccharose, Isomalt, cyclodextrins such as α-cyclodextrins, β-cyclodextrins, γ-cyclodextrins and hydroxyl-propyl-β-cyclodextrins, sodiumcarboxymethylcellulose, sodium alginate, xantham gum, caavageenan, locust bean gum (*ceratonia*), chitosan, guar gum, cross-linked high amylase starch, and cross-linked polyacrylic acid (carbopol).

3. The amorphous solid dispersion of mirabegron of claim 2, wherein the pharmaceutically acceptable carrier is one or more of copovidone.

4. The amorphous solid dispersion of mirabegron of claim 2, wherein the pharmaceutically acceptable carrier is one or more of hypromellose acetate succinate (HPMC AS).

5. The amorphous solid dispersion of mirabegron of claim 2, wherein the pharmaceutically acceptable carrier is one or more of hydroxypropylcellulose (HPC).

6. The amorphous solid dispersion of mirabegron of claim 1, wherein the ratio of one or more pharmaceutically carrier to the mirabegron is at least about 1:2 (w/w) to about (2:1) (w/w).

7. The amorphous solid dispersion of mirabegron of claim 1, further comprising one or more antioxidant.

8. The amorphous solid dispersion of mirabegron of claim 7, wherein one or more antioxidant is selected from butylated hydroxytoluene (BHT), butyl hydroxy anisole (BHA), DL-α-tocopherol, propyl gallate, ascorbyl palmitate, malonic acid, and fumaric acid.

9. The amorphous solid dispersion of mirabegron of claim 1, further comprising a stabilizer.

10. The amorphous solid dispersion of mirabegron of claim 9, wherein the stabilizer is amorphous silica.

11. A solid pharmaceutical formulation comprising amorphous solid dispersion of mirabegron according to claim 1, and one or more pharmaceutically acceptable excipient.

* * * * *